Figure 1:
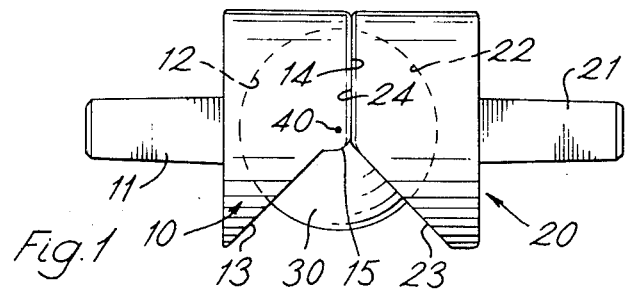
Figure 2:
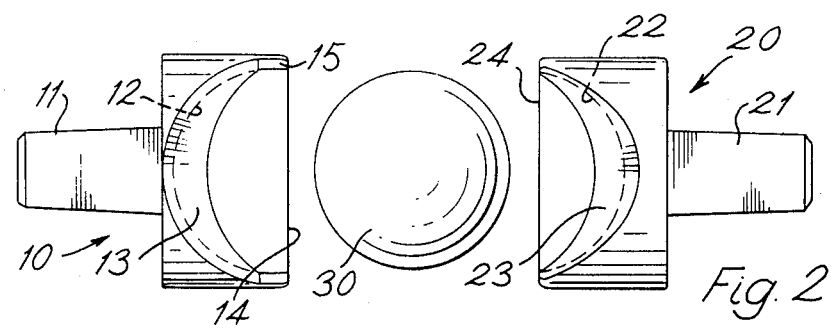
Figure 3:
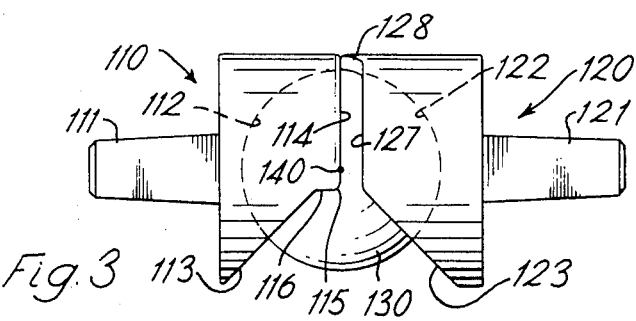
Figure 4:
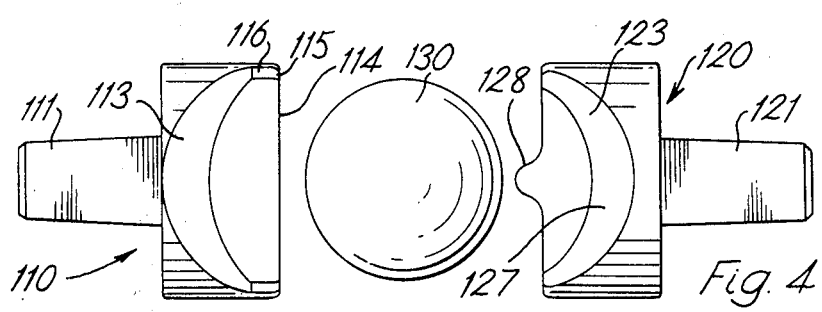

United States Patent [19]
Freeman et al.

[11] 3,992,726
[45] Nov. 23, 1976

[54] ENDOPROSTHETIC BONE JOINT DEVICES

[75] Inventors: Michael Alexander Reykers Freeman, London; Michael Anthony Tuke, Sutton, both of England

[73] Assignee: National Research Development Corporation, London, England

[22] Filed: July 30, 1975

[21] Appl. No.: 600,475

[30] Foreign Application Priority Data
Aug. 7, 1974   United Kingdom............... 34812/74

[52] U.S. Cl. ................................. 3/1.91; 128/92 C
[51] Int. Cl.² ........................................... A61F 1/24
[58] Field of Search ............................ 3/1.9–1.913, 3/1; 128/92 C, 92 CA

[56] References Cited
UNITED STATES PATENTS
3,608,096   9/1971   Link....................................... 3/1.912
3,651,521   3/1972   Devas..................................... 3/1.91

FOREIGN PATENTS OR APPLICATIONS
426,096   6/1967   Switzerland.......................... 3/1.912

Primary Examiner—Ronald L. Frinks
Attorney, Agent, or Firm—Cushman, Darby & Cushman

[57] ABSTRACT

An endoprosthetic bone joint device, particularly suitable for a finger or toe joint, comprises two cups and a ball or other roller freely located in and between the cups in articulatory engagement. Normally the cups do not wholly encompass the ball, and so allow flexion-extension simulating articulation limited by mutual abutment of relevant portions of the cup rims. For this purpose, at least one of the cup rims is contoured from planar form to provide two mutually-inclined, diametrically-opposed stop surfaces. Various requirements for abduction-adduction function simulation can also be accommodated by curved profiling of said one cup rim between its stop surfaces.

8 Claims, 6 Drawing Figures

U.S. Patent  Nov. 23, 1976  Sheet 1 of 2  3,992,726

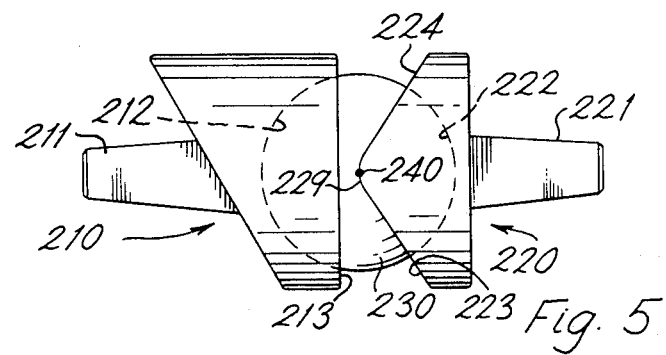
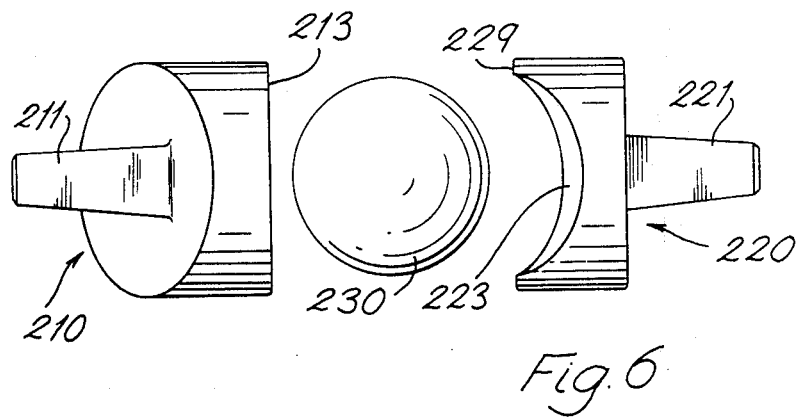

ENDOPROSTHETIC BONE JOINT DEVICES

This invention concerns prosthetic devices and more particularly endoprosthetic bone joint devices.

The invention has been developed initially in relation to the matatarsal-phalangeal joint of the big toe to provide an improved basis for the surgical treatment of bunions, which treatment retains an articulation capability in the relevant joint. There appeared to be no suitable commercially-available device for this purpose, and the currently conventional surgical treatment involves fusion of the joint, or excision of the joint surfaces.

However, the invention is not limited to this practical application since, as will be seen, the invention provides a device which is relatively simple in form and function, and this device is readily modified to suit the requirements of other joints, particularly those of the fingers.

In a more general aspect, the invention provides an endoprosthetic bone joint device comprising first and second components each in the form of a cup having its exterior surface adapted for securement to a respective bone of the relevant joint, and a third component in the form of a roller freely locatable in and between said cups in articulatory engagement therewith.

Normally the roller will be of ball form, and more usually this will be a spherical ball, with the cups having spherically-shaped interior surfaces of equal radius, and the cup interior surfaces together subtending a total solid angle at their spherical centres which is less than that of a sphere. A simpler expression of this last feature is that the cup interior surfaces are not sufficiently extensive that the cup rims are substantially complementary and permanently wholly engaged, but on the contrary the rims can be spaced apart to allow mutual articulation between the cups relative to the ball, such articulation occuring between limiting configurations in which the cup rims engage each other.

In this last connection, the cups will nomally be such that at least one cup has a rim which is contoured to provide two mutually-inclined, diametrically-opposed stop surfaces which abut the rim of the other cup to limit articulation in the opposite senses of a predetermined direction. In practice, the articulation just referred to will usually be that corresponding to flexion-extension movement in the related natural joint.

Also, it will sometimes be appropriate that a cup having such stop surfaces has its rim profiled to provide two similarly curved surfaces continuing from the respective ends of one of the stop surfaces, such curved surfaces serving to rollingly and/or slidably engage the rim of the other cup and inhibit articulation in a direction transverse to said predetermined direction. Such curved surfaces are appropriate to devices for natural joints in which there is no abduction-adduction function during at least part of the flexion-extension range of movement. In the case where there is no such function, as in an interphalangeal joint, for example, the curved surfaces will extend completely between the stop surfaces. In the case where there is some abduction-adduction capability during part of the flexion-extension range, such as with the metacarpal-phalangeal joint, the curved surfaces extend only partway from one stop surface towards the other.

In order to provide a fuller understanding of the possibilities of practical application of the present invention, the invention will now be described by way of example with reference to the accompanying drawings, in which:

FIGS. 1 and 2, and 3 and 4, and 5 and 6 respectively diagrammatically illustrate, in mutually perpendicular assembled and exploded side views, three different embodiments of the invention applicable to different joints.

The first embodiment is applicable to an interphalangeal joint having a flexion-extension function but no abduction-adduction function. This embodiment comprises first and second components 10 and 20 each in the form of a cup with its exterior surface adapted for securement to a phalangeal bone by the provision of a respective intramedullary stem 11, 21 extending therefrom. The interior surfaces 12, 22 of the cups are spherically shaped to the same radius, but do not have substantially complementary rims.

The rim of the cup 10 is comprised of two stop surfaces 13, 14 and two curved surfaces 15 of which only one is shown. The stop surfaces are each of planar form, and they are mutually-inclined to define an obtuse angle therebetween, the surface 13 being radial, and the surface 14 being chordal in a major segmental plane. Also, the surfaces 13, 14 are diametrically-opposed on the relevant cup rim. The curved surfaces are convexly circularly curved in like manner as seen in side elevation and extend fully between respective adjacent ends of the surfaces 13, 14.

The rim of the cup 20 is simpler than that of cup 10, the former being comprised of just two stop surfaces 23, 24 which are of mutually-inclined, diametrically-opposed, respectively radial and chordal planar form defining an obtuse angle therebetween, the latter surface being in a minor segmental plane.

The third component of FIG. 1 is a spherical ball 30 of the same radius as the cup interior surfaces 12, 22 whereby the cups can engage the ball in opposed manner. This engagement allows mutual articulation between the cups relative to the ball only in the plane of FIG. 1, such articulation being limited in one sense by abutment between the stop surfaces 13 and 23, and in the other sense by abutment of stop surfaces 14 and 24. Articulation between the cups in any transverse sense relative to and during the range of that just mentioned is inhibited by sliding engagement of the curved surfaces 15 with the stop surface 24.

The stems 11 and 21 are orientated with their longitudinal axes perpendicular to the respectively associated stop surfaces 14 and 24 so that, in use, the latter surfaces abut in a configuration corresponding to full extension and the surfaces 13 and 23 similarly abut at full flexion. Also, it is intended that the stems 11 and 21 be respectively secured in the proximal and distal bones of the relevant joint, such securement being effected by the use of acrylic cement or equivalent gap-filling medium.

The common spherical centre of the cups and ball, when assembled, is denoted at 40.

Turning to the second embodiment: this is applicable to a metacarpal-phalangeal joint, which has a flexion-extension function with an abduction-adduction capability during only part of the range of the former function.

For convenience, parts of this second embodiment representing corresponding or similar features to those of the first embodiment are denoted by the same reference numerals but with a one hundred digit added. Thus the second embodiment has proximal first and distal second cup components 110, 120 with respective stems 111, 121 and with respective spherically shaped interior surfaces 112, 122 of the same radius for mutual articulatory engagement with a complementary ball 130 therebetween. The common spherical centre is denoted at 140.

The rim of the cup 110 has two mutually-inclined diametrally-opposed planar surfaces 113, 114 which are respectively minor-segmentally chordal and radial, and two circularly curved surfaces 115 which extend from the respective ends of stop surface 114 partway towards adjacent ends of stop surface 113. The curved surfaces 115 are joined with the stop surface 113 by way of two further planar stop surfaces 116 which are mutually inclined with both stop surfaces 113 and 114.

The rim of the cup 120 has a planar stop surface 123 in a major segmental plane, which surface co-operates with stop surface 113, two planar surfaces 127 extending in a minor segmental plane in like manner from respective ends of stop surface 123 and which co-operate in part with the curved surfaces 115 and stop surface 116, and a convexly curved surface 128 joining the planar surfaces 127 and co-operating with stop surface 114. Surface 128 extends maximally to the radial plane parallel with surfaces 127.

In the operation of this second embodiment the rim surfaces 114 and 128 engage as shown to limit flexion-entension articulation in a configuration corresponding to full extension with the longitudinal axes of the stems 111 and 121 aligned. However, the curvature of the surface 128 allows the same to slide transversely on the surface 114 and provide an abduction-adduction capability in the last-mentioned configuration, this capability being limited by engagement of corresponding surfaces 114 and 127. Moreover, this capability is retained during that part of the flexion-extension function range of movement between the illustrated full extension configuration and the partially flexed configuration when surface 115 engages surface 127. Once the latter engagement occurs, the remaining flexion-extension movement range involves continued sliding engagement of the surfaces 115 and 127 to inhibit abduction-adduction. Finally, at full flexion the stop surfaces 113 and 123 abut, and stop surface 116 also abuts with the end portions of surfaces 127 adjoining stop surface 123.

Considering now the third embodiment: this is applicable to a metatarsal-phalangeal joint and represents the initial development of the present invention in respect of the big toe. The natural joint has a flexion-extension capability comprising dorsoplantar movement, and also has a slight abduction-adduction capability.

Again it is convenient to retain corresponding reference numerals to the first embodiment where appropriate, with the addition of a two hundreds digit in this instance. Thus, the third embodiment has proximal first and distal second cup components 210, 220 with respective stems 211, 212 and with respective spherically shaped interior surfaces 212, 222 of the same radius for mutual articulatory engagement with a complementary ball 230 therebetween. The common spherical centre is denoted at 240.

The rim of the cup 210 is comprised of a single planar stop surface 213 in a minor segmental plane, while that of cup 220 has two mutually-inclined, diametrally-opposed, planar surfaces 223 and 224 in major segmental planes with adjacent pairs of ends thereof respectively joined through circularly curved surfaces 229.

When the cup rims are symmetrically disposed in spaced relation in the illustrated zero-flexion configuration, flexion-extension movement can occur in both senses with such movements being limited by respective engagement of the stop surfaces 223 and 224 with the stop surface 213. In addition, it will be seen that an abduction-adduction movement is possible during flexion-extension, such movement being limited by engagement of surface 229 with surface 213. More particularly, the range of the latter movement varies progressively from zero to a maximum as the cups are in a configuration varying from full flexion, in one sense or the other, to zero flexion. These variations are best appreciated by visualizing the cup 220 moved to roll its rim around that of cup 210, such rolling being possible through a complete cycle by virtue of the curved surfaces 229.

While the invention has been described with more particular reference to the three illustrated embodiments, they are specifically stated to be exemplary and diagrammatic and, as such, they are capable of modification. For example, the embodiments illustrate different modes of profiling the cup rims to allow different articulating capabilities and it is clearly possible to produce further variations of profiles to meet a given requirement. One example of such a requirement arises from the possible desire to inhibit a capability for articulation in the device by relative rotation about the longitudinal axes of the stems in the third embodiment when in a configuration corresponding to substantially full dorsiflexion. This can be effected by the provision of a notch in the top of the rim surface 213 and a projection from the top of the rim surface 224 for receipt in this notch, the notch and projection being suitably tapered to ensure engagement therebetween as dorsiflexion occurs.

Also, the exterior form of the cups can be modified to suit different requirements. This will normally be the case insofar as a cup will preferably blend with the adjacent external form of the bone to which it is secured. Also, it may be appropriate to provide throughed formations to receive and laterally stablize ligaments. Similarly the cup exterior form adjacent the root of its stem can vary to suit abutment with different sections appropriate to differing surgical techniques with different joints. This is apparent from comparison of the embodiments in which all cups have a planar surface which is perpendicular to the associated stem in side view except for the metatarsal component of FIG. 5 in which the corresponding surface is inclined. Modification can also be made in respect of the relative inclination of the stems insofar as these need not necessarily be longitudinally aligned when the cup rims are mutually symmetrically disposed. For example, application of the third embodiment to the big toe preferably involves such longitudinal alignment as seen in side view, but mutual inclination at about 160° as seen in plan view, such inclination best being applied to component 220 so that the device can still be used, one way up or the other, for a left or right foot. Lastly regarding the exterior form of the cups, it is currently preferred to employ intramedullary stems for securement, but alternative features are possible, such as low relief configurations as used in other endoprosthetic bone joint devices.

Modification can also be made, as intimated in the introductory discussion, in the ball insofar as this can be, more generally, a roller. Thus, a substantially cylindrical roller is appropriate to situations such as that of an interphalangeal joint having a single articulation capability, namely flexion-extension. Naturally, other roller shapes such as barrel or ellipsoid shapes are also possible, it being understood that the cup interior surfaces also will be appropriately modified.

Another possibility for modification lies in the fact that the ball or roller can be connected with, or integrally formed with one of the cup components.

A further possibility for variation lies in the choice of materials. At present an optimum choice appears to be the use of a plastics material such as ultra high molecular weight polyethylene for the cups, and a metal such as stainless steel for the ball. This choice offers the known advantages of metal-plastic combinations of components, including low friction, while at the same time simplifying manufacture. This simplification arises from the fact that metal balls and rollers can be obtained to satisfactory tolerances and standards of surface finish for the present purpose by way of existing techniques in ball and roller bearing manufacture. The remaining, more complex cup components are readily machined from the more easily worked plastics material, and the overall result is one of economy compared to existing two-component metal-plastic endoprosthetic bone joint devices. Moreover, this economy is enhanced by the fact that a given size of ball can be employed for a range of the presently proposed devices for different joints.

However, notwithstanding this preference, other materials and combinations thereof can clearly be employed. For example, it may be desired to employ a metal rim for a cup such as the simple cup 210 to provide metal-plastic in respect of both ball-cup and cup-cup engagements.

Lastly, in manufacture, it is desirable to make the ball or other roller as large as possible compatible with the cups being appropriate to the relevant joint size and the loads to be borne in the cups and between their rims when engaged. As the roller is larger so a larger bearing surface area is provided in the device and a better simulation of such overall profiles as that of a knuckle.

We claim:

1. An endoprosthetic bone joint device comprising: first and second components each in the form of a cup having its exterior surface adapted for securement to a respective bone of the relevant joint, and a third component in the form of a roller freely located in and between said cups in articulatory engagement therewith,
at least one of said cups having a rim which is contoured to provide two mutually-inclined stop surfaces which individually abut the rim of the other cup to respectively limit articulation in the opposite senses of a predetermined direction, and
said one cup rim being profiled to provide two similarly curved surfaces continuing from respective ends of one of said stop surfaces, which curved surfaces rollingly and slidingly engage said other cup rim to inhibit articulation in a direction transverse to said predetermined direction.

2. A device according to claim 1 wherein said roller is a spherical ball, the interior surfaces of said cups are spherically shaped, said interior surfaces subtend a total solid angle at their common spherical centre which is less that that of a sphere, and said stop surfaces are diametrally-opposed on said one cup rim.

3. A device acccording to claim 2 wherein the other of said cups has a rim which is contoured to provide two mutually-inclined, diametrically-opposed stop surfaces which respectively abut said one cup stop surfaces to limit articulation in the opposite senses of said predetermined direction.

4. A device according to claim 3 wherein all of said stop surfaces are planar.

5. A device according to claim 3 wherein one of said other cup stop surfaces is of convexly curved form, and the respective one of said one cup stop surfaces is planar.

6. A device according to claim 4 wherein said one cup stop surfaces are respectively located in major segmental and radial planes relative to the relevant cup interior surface, and said other cup stop surfaces are respectively located in minor segmental and radial planes relative to the relevant cup interior surface.

7. A device according to claim 5 wherein: said one cup stop surfaces are respectively located in radial and minor segmental planes relative to the relevant cup interior surface; and said other cup stop surfaces comprises a convexly curved surface portion extending maximally to a radial plane from a minor segmental planar surface portion, and a planar surface located in a major segmental plane, relative to the relevant cup interior surface.

8. A device according to claim 2 wherein said one cup stop surfaces are planar, and said other cup rim is substantially wholly planar.

* * * * *